United States Patent
Neugebauer et al.

(10) Patent No.: US 6,462,242 B1
(45) Date of Patent: Oct. 8, 2002

(54) PROCESS FOR PREPARING BENZYL ALCOHOLS AND THEIR USE

(75) Inventors: Torsten Neugebauer, Cambridge, MA (US); Albrecht Marhold, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/587,742

(22) Filed: Jun. 5, 2000

(30) Foreign Application Priority Data

Jun. 11, 1999 (DE) .......................... 199 26 621

(51) Int. Cl.$^7$ .............................................. C07C 33/46
(52) U.S. Cl. ................. 568/812; 564/375; 568/814; 568/649; 568/428
(58) Field of Search .................. 568/812, 814, 568/428, 649; 564/375

(56) References Cited

U.S. PATENT DOCUMENTS

| | | | | |
|---|---|---|---|---|
| 3,089,826 A | * | 5/1963 | Sahyun | |
| 3,527,817 A | * | 9/1970 | Dietzler | |
| 3,983,122 A | * | 9/1976 | Lundberg | |
| 3,988,454 A | * | 10/1976 | Christy | |
| 4,118,561 A | | 10/1978 | Ledig | .......... 542/470 |
| 4,605,749 A | * | 8/1986 | Buchman | |
| 4,933,497 A | * | 6/1990 | Fompeyrine | |
| 4,942,240 A | * | 7/1990 | Bluthe | |
| 4,978,801 A | * | 12/1990 | Bluthe | |
| 5,126,492 A | * | 6/1992 | Milstein | |
| 5,387,726 A | * | 2/1995 | Bankman | |
| 5,498,612 A | | 3/1996 | Obata et al. | ............. 514/256 |
| 6,020,517 A | * | 2/2000 | Monzen | |
| 6,127,581 A | * | 10/2000 | Wiedemann | |

FOREIGN PATENT DOCUMENTS

JP     8-291149     11/1996

OTHER PUBLICATIONS

Bull. Chem. Soc. Jpn., 67 pp. 2329–2332, (month unavailable) 1994, Okano et al, Formylation of Aryl Halides with Carbon Monoxide and Sodium Formate in the Presence of Palladium Catalyst.

J. Med. Chem., vol. 18, No. 12, (month unavailable) 1975, p. 1216, Herrin et al, Antimalarials. Synthesis of Antimalarial Activity of 1–(4–Methoxycinnamoyl)–4–(5–phenyl–4–oxo–2–oxazolin–2yl)piperazine (only p. 1216 provided).

Ullmann's Ency. of Ind. Chem. vol. A17, 5$^{th}$ ed. (month unavailable) 1991, p. 372, Nitriles.

Beisteins Handbuch der Organischen Chemie, 4$^{th}$ edition (month unavailable) 1984, vol. E IV 12, p. 2453, Phenäthylamin.

* cited by examiner

*Primary Examiner*—Michael L. Shippen
(74) *Attorney, Agent, or Firm*—Joseph C. Gil; Diderico van Eyl

(57) ABSTRACT

Benzyl alcohols, particularly those which bear fluorine substituents or fluoroalkyl substituents on the benzyl ring, can be obtained by formylation of corresponding aryl bromides to form benzaldehydes and reduction of the latter using further formate, wherein the benzaldehydes formed do not have to be isolated.

18 Claims, No Drawings

PROCESS FOR PREPARING BENZYL ALCOHOLS AND THEIR USE

BACKGROUND OF THE INVENTION

The present invention relates to a process for preparing benzyl alcohols by formylation of aryl bromides to form benzaldehydes and reduction of the latter using a formate.

The formylation of aryl bromides by means of carbon monoxide in the presence of sodium formate and a palladium catalyst at atmospheric pressure is already known (Bull. Chem. Soc. Jpn., 67, 2329–2332, 1994). The corresponding benzaldehydes can in some cases be obtained in very good yields. However, no mention is made of the formation of benzyl alcohols.

Although various methods of synthesizing benzyl alcohols are known, there is no general route available which could advantageously be used for the industrial production of a wide variety of substituted benzyl alcohols. This is particularly true of the preparation of benzyl alcohols which bear fluorine substituents or fluorine-containing substituents on the aromatic ring.

For example, U.S. Pat. No. 4,118,561 teaches the preparation of 4-(trifluoromethoxy)benzoic alcohol by the reduction of 4-(trifluoromethoxy) benzoic acid using lithium alanate. In J. Med. Chem. 18, 1216, 1975, the reduction of 4-(trifluoromethoxy)benzoic acid using diborane is described. Carrying out reductions using lithium alanate or diborane on an industrial scale would require a considerable outlay in terms of safety measures.

Benzyl alcohols are used, inter alia, in the production of surface coatings and flavorings and can be used for the preparation of phenethylamines. Phenethylamines bearing fluorine substituents or fluorine-containing substituents such as 4-(trifluoromethoxy)-phenethylamine, are interesting intermediates in applications such as for agrochemicals (EP 00 665 225 or JP 08 291 149).

In view of the foregoing, there is a need for a simple and safe process for preparing benzyl alcohols having a widely variable substitution pattern, particularly those bearing fluorine substituents or fluorine-containing substituents.

DESCRIPTION OF THE INVENTION

We have now found a process for preparing benzyl alcohols of the formula (I)

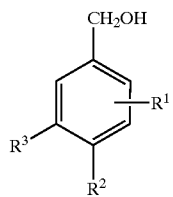

(I)

in which $R^1$, $R^2$ and $R^3$ are, in each case independently of one another, H, F, Cl, $NO_2$, straight-chain or branched $C_1$–$C_{12}$-alkyl groups, phenyl groups, OH groups, $O(CH_2)_nCH_3$ groups wherein n=0–12, $(CF_2)_nCF_3$ in which n=0–2 or $O(CX_2)_nCX_3$ in which n =0–12, and X represents F and/or Cl. The process is characterized in that aryl bromides of the general formula (II),

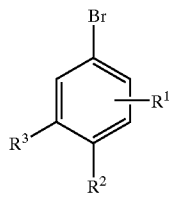

(II)

wherein $R^1$, $R^2$, $R^3$ are as defined for formula (I), are reacted with carbon monoxide and a formate in the presence of a palladium catalyst to form benzaldehydes of the formula (III)

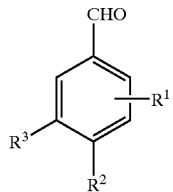

(III)

wherein $R^1$, $R^2$ and $R^3$ are as defined for formula (I), in which the benzaldehydes of the formula (III) obtained in this way are reduced to the corresponding benzyl alcohols. The benzaldehydes of the formula (III) which are formed can, if desired, be isolated, purified and reduced in a second step.

In formulas (I), (II), (III) and (IV) $R^1$ is preferably in meta-position with respect to the $CH_2OH$—, Br—, CHO— or $CH_2$—$CH_2$—$NH_2$-group respectively.

The reduction to benzyl alcohols of the formula (I) can be carried out using formate in the presence of a palladium catalyst. Alternatively, the benzaldehyde formed can also be reduced by means of hydrogen in an autoclave at temperatures of at least about 60° C. from 60° C. to 120° C. and pressures of from 30 bar to 70 bar in the presence of a palladium catalyst to give the benzyl alcohol. Reduction with hydrogen is an interesting alternative, particularly when benzyl alcohols of the formula (1), in which at least one of the radicals $R^1$, $R^2$ or $R^3$ is F, $CF_3$, $CF_2CF_3$, $CF_2CF_2CF_3$ or $O(CX_2)_nCX_3$, in which n=0–12 and X=F and/or Cl, are to be prepared, e.g., 4-trifluoromethoxy-benzyl alcohol.

However, the process of the invention is preferably carried out as a single-vessel reaction in which the benzaldehydes of the formula (III) formed in the first step are reacted directly, without intermediate work-up, with formate over a palladium catalyst to give benzyl alcohols of the formula (I). This procedure avoids purification steps at the benzaldehyde stage, which significantly reduces the complication of the synthesis in comparison with two-stage processes and thus makes this procedure very interesting for process-engineering and economic reasons.

The formate employed can be used, for example, in the form of the ammonium, lithium, potassium, sodium, caesium, calcium or barium salt or can be generated in situ, for example from triethylamine and formic acid. The use of potassium, sodium or ammonium formate is preferred.

To carry out the process of the invention, a palladium catalyst is used. Palladium is advantageously used in the oxidation state 0 or II. With respect to catalysts in which palladium is present in the oxidation state 0, it is possible to use complexes such as palladium complexes that have substituted or unsubstituted triphenylphosphine ligands. An example which may be mentioned is tetrakistriphenylphosphine-palladium (0).

Catalysts in which palladium is present in the oxidation state II can be used in the form of palladium (II) salts in combination with suitable free ligands or in the form of palladium(II) complexes.

Suitable palladium(II) complexes include compounds such as those of the general formula $$L_2PdX_2 \text{ or } L^1PdX_2,$$

in which

L represents a phosphine bearing substituted or unsubstituted, branched or unbranched $C_1$–$C_{10}$-alkyl and/or substituted or unsubstituted $C_6$–$C_{10}$-aryl radicals, $L^1$ represents a chelating ligand of the formula $R^4{}_2P(CH_2)_n PR^4{}_2$, in which $R^4$=substituted or unsubstituted, branched or unbranched $C_1$–$C_{10}$-alkyl or substituted or unsubstituted $C_6$–$C_{10}$-aryl and n=1–4, and X represents Cl, Br, I, acetate, dibenzylideneacetone and/or nitrate.

Examples of ligands L include $PPh_3$, $P(2\text{---}MeC_6H4)_3$, $P(_4\text{---}MeC_6H_4)_3$, $P(4\text{---}MeOC_6H_4)_3$, $P(4\text{---}ClC_6H_4)_3$, $P(cyclohexyl)_3$, $PMe_2Ph$, $PPh_2Me$, $PPh_2(CH(CH_3)_2)$, $PEt_3$, $PMe_3$, $P(CH(CH_3)_2)_3$ and $P(C(CH_3)_3)_3$. Here, the two ligands L can, in each case, be selected independently of one another. However, it is advantageous for the two ligands L to be identical.

Examples of chelating ligands $L^1$ include $(C_6H_5)_2PCH_2P(C_6H_5)_2$, $(C_6H_5)_2P(CH_2)_2P(C_6H_5)_2$, $(C_6H_5)_2P(CH_2)_3P(C_6H_5)_2$ and 1,1'-bis(diphenylphosphino, ferrocene.

As palladium(II) salts in combination with free ligands L or $L^1$, wherein L and $L^1$ are as defined above, it is possible to use, for example, palladium(II) halides, in particular, palladium(II) chloride, palladium(II) acetylacetonate, $Pd(CN)_2$, $Pd(CH_3CN)Cl_2$, $Pd(C_6H_5CN)Cl_2$, palladium(II) 1,1,1,5,5,5-hexafluoroacetylacetonate and palladium(II) acetate.

The process of the invention is advantageously carried out at temperatures of at least about 80° C., for example from about 80° C. to about 140° C., preferably at temperatures of from 105° C. to 115° C.

The reaction pressure is not critical. If the reaction is to be carried out at high temperatures using low-boiling solvents, an autoclave can be used. However, the reaction is advantageously carried out in a pressure range from at least about 1 bar, preferably from about 1 to 10 bar. In a preferred embodiment, carbon monoxide is passed into the reaction mixture in such a way that the reaction pressure is approximately atmospheric pressure (1 bar to 1.2 bar). Such reaction conditions place low demands on the pressure resistance of the reactor used. Accordingly, many reactors are suitable for carrying out the process of the invention.

If the aryl bromides used are liquid under the reaction conditions, the process of the invention can be carried out without addition of a solvent. However, it is advantageously carried out in a polar, aprotic, organic solvent, for example, dimethylformamide, N-methylpyrrolidone, dimethylacetamide, pyridine, 1,3-dimethyl-imidazolidin-2-one, dimethyl sulfoxide, toluene, xylene, acetonitrile, propionitrile, benzonitrile or chlorobenzene or mixtures thereof Preferred solvents are dimethylformamide, N-methylpyrrolidone and dimethylacetamide.

The process of the invention can be carried out, for example, by placing the aryl bromide to be reacted together with a palladium catalyst and a formate in a reaction vessel, adding an inert solvent to this mixture and reacting it while passing in CO at atmospheric pressure and elevated temperature to form firstly the benzaldehyde. Subsequently, the introduction of CO is stopped and the benzaldehyde is allowed to react further to form the benzyl alcohol.

Surprisingly, the process of the invention allows aryl bromides to be converted into benzyl alcohols by reaction with carbon monoxide and formate, a very weak reducing agent, in a single-vessel reaction, while the mixture of carbon monoxide and formate has hitherto been used only for preparing benzaldehydes from aryl bromides.

The process of the invention is particularly advantageous for preparing benzyl alcohols of the formula (I) in which at least one of the radicals $R^1$, $R^2$ or $R^3$ is F, $CF_3$, $CF_2CF_3$, $CF_2CF_2CF_3$ or $O(CX_2)_nCX_3$, wherein n=0–12 and X=F and/or Cl, in particular for preparing 4-trifluoromethoxybenzyl alcohol.

The benzyl alcohols of the formula (I), prepared according to the invention can be used for preparing phenethylamines of the formula (IV)

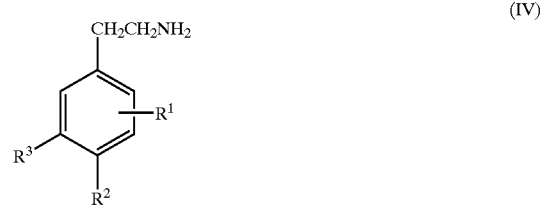

(IV)

wherein $R^1$, $R^2$ and $R^3$ are as defined for formula (I).

Suitable reagents and reaction conditions are known to those skilled in the art. The benzyl alcohols prepared according to the invention can, as described, for example, in U.S. Pat. No. 4,118,561, be firstly reacted with a customary halogenating reagent, for instance, thionyl chloride, to give benzyl halides. The latter can be converted into benzyl cyanides by, for instance, reaction with alkali metal cyanide (cf Ullmann's Encyclopedia of Industrial Chemistry, Vol. A17, 5th edition, 1991, p. 372) and these can finally be converted into phenethylamines of the formula (V) by hydrogenation, for example, using lithium alanate and aluminium trichloride or hydrogen in the presence of a cobalt catalyst (Beilsteins Handbuch der Organischen Chemie, 4th edition 1984, volume E IV 12, p. 2453).

The invention provides previously unavailable advantages, notably a simple and safe process for preparing benzyl alcohols having a widely variable substitution pattern. The invention is especially suitable for preparing benzyl alcohols bearing fluorine substituents or fluorine-containing substituents.

The invention is further illustrated but is not intended to be limited by the following examples in which all parts and percentages are by weight unless otherwise specified.

EXAMPLES

Example 1

4-Trifluoromethoxybenzaldehyde 3.62 g of 4-trifluoromethoxybromobenzene, 0.21 g of bis(triphenylphosphine)palladium dichloride and 1.53 g of sodium formate were placed in a flask fitted with a reflux condenser and a gas inlet tube, 15 ml of DMF were added and the mixture was stirred and heated at 110° C. while passing in CO. After conversion was complete (GC monitoring), the reaction mixture was allowed to cool to 21° C. and the catalyst was separated off by filtration through silica gel.

This gave a crude product containing 91% of 4-trifluoromethoxy-benzaldehyde and 7% of 4-trifluoromethoxy-benzyl alcohol (percentages are based on the areas in the GC).

Example 2

4-Trifluoromethylbenzaldehyde 3.38 g of 4-trifluoromethylbromobenzene, 0.21 g of bis(triphenylphosphine)palladium dichloride and 1.53 g of sodium formate were placed in a flask fitted with a reflux condenser and a gas inlet tube, 15 ml of DMF were added and the mixture was stirred and heated at 110° C. while passing in CO. After conversion was complete (GC monitoring), the reaction mixture was allowed to cool to 21° C. and the catalyst was separated off by filtration through silica gel.

This gave a crude product containing 91% of 4-trifluoromethyl-benzaldehyde and 8% of 4-trifluoromethylbenzyl alcohol (percentages are based on the areas in the GC).

Example 3

3,4-Difluorobenzaldehyde 2.90 g of 3,4-difluorobromobenzene, 0.21 g of bis(triphenylphosphine)palladium dichloride and 1.53 g of sodium formate were placed in a flask fitted with a reflux condenser and a gas inlet tube, 15 ml of DMF were added and the mixture was stirred and heated at 110° C. while passing in CO. After conversion was complete (GC monitoring), the reaction mixture was allowed to cool to 21° C. and the catalyst was separated off by filtration through silica gel.

This gave a crude product containing 95% of 3,4-difluoro-benzaldehyde and 4% of 3,4-difluorobenzyl alcohol (percentages are based on the areas in the GC).

Example 4

2-Fluoro-4-methylbenzaldehyde 2.84 g of 2-fluoro-4-methylbromobenzene, 0.21 g of bis(triphenylphosphine)palladium dichloride and 1.53 g of sodium formate were placed in a flask fitted with a reflux condenser and a gas inlet tube, 15 ml of DMF were added and the mixture was stirred and heated at 110° C. while passing in CO. After conversion was complete (GC monitoring), the reaction mixture was allowed to cool to 21° C. and the catalyst was separated off by filtration through silica gel.

This gave a crude product which contained >95% of 2-fluoro-4-methylbenzaldehyde and <1% of 2-fluoro-4-methylbenzyl alcohol (percentages are based on the areas in the GC).

Example 5

4-Trifluoromethoxybenzyl Alcohol 8.55 g of 4-trifluoromethoxybenzaldehyde, 0.63 g of bis(triphenylphosphine) palladium dichloride and 6.12 g of sodium formate were placed in a flask fitted with a reflux condenser, 45 ml of DMF were added and the mixture was stirred and heated at 110° C. The course of the reaction was monitored by means of GC. After conversion was complete (GC monitoring), the reaction mixture was allowed to cool to 21° C. and the catalyst was separated off by filtration through silica gel. The filter was rinsed with methyl tert-butyl ether and the filtrate washed with 3×100 ml of water in order to remove the DMF. This gave 6.0 g (69% of theory) of 4-trifluoromethoxybenzyl alcohol.

Example 6

3,5-Bis-(trifluoromethyl)-benzaldehyde 4.40 g of 3,5-bis-(trifluoromethyl)-bromobenzene, 0.21 g of bis(triphenylphosphine)-palladium dichloride and 1.53 g of sodium formate were placed in a flask fitted with a reflux condenser and a gas inlet tube, 15 ml of DMF were added and the mixture was stirred and heated at 110° C. while passing in CO. After conversion was complete (GC monitoring), the reaction mixture was allowed to cool to 21° C. and the catalyst was separated off by filtration through silica gel.

This gave a crude product which contained 43% of 3,5-bis-(trifluoromethyl)-benzaldehyde and 57% of 3,5-bis-(trifluoromethyl)benzyl alcohol (percentages are based on the areas in the GC).

Example 7

4-Fluoro-3-methyl-benzaldehyde 2.85 g of 5-bromo-2-fluorotoluene, 0.21 g of bis(triphenyl-phosphine)palladium dichloride and 1.53 g of sodium formate were placed in a flask fitted with a reflux condenser and a gas inlet tube, 15 ml of DMF were added and the mixture was stirred and heated at 110° C. while passing in CO. After conversion was complete (GC monitoring), the reaction mixture was allowed to cool to 21° C. and the catalyst was separated off by filtration through silica gel.

This gave a crude product which contained >98% of 4-fluoro-3-methyl-benzaldehyde (percentage is based on the areas in the GC). No starting material could be detected.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing benzyl alcohols of formula (I)

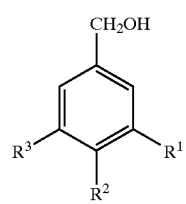

(I)

wherein each $R^1$, $R^2$ and $R^3$ is a member selected from the group consisting of H atoms, F atoms, Cl atoms, $NO_2$ groups, straight-chain or branched $C_1$–$C_{12}$-alkyl groups, phenyl groups, OH groups, $O(CH_2)_nCH_3$ groups, in which n=0–12, $(CF_2)_nCF_3$, in which n=0–2 or $O(CX_2)_nCX_3$, in which n=0–12, and X represents F and/or Cl;

the process comprising:

(A) reacting (1) aryl bromides of the general formula (II),

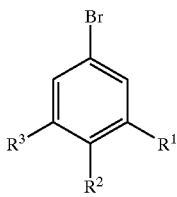

(II)

wherein $R^1$, $R^2$, $R^3$ are as defined for formula (I), with
(2) carbon monoxide and a formate in the presence of a palladium catalyst to form benzaldehydes of formula (III)

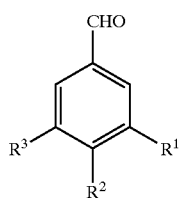

(III)

wherein $R^1$, $R^2$ and $R^3$ are as defined for formula (I), and (B) reducing the benzaldehydes of formula (III) to the corresponding benzyl alcohols, wherein the step of reducing the benzaldehydes of formula (III) is carried out using additional formate in the presence of a palladium catalyst.

2. The process of claim 1, wherein the formate is in the form of its ammonium salt, lithium salt, potassium salt, sodium salt, caesium salt, calcium salt or barium salt or is generated in situ.

3. The process of claim 1, wherein the catalyst is tetrakistriphenyl-phosphine-palladium(0).

4. The process of claim 1, wherein the catalyst is a palladium complex of the general formula $L_2PdX_2$, wherein L represents a member selected from the group consisting of phosphine bearing substituted $C_1$–$C_{10}$-alkyl groups, phosphine bearing unsubstituted $C_1$–$C_{10}$-alkyl groups, substituted $C_6$–$C_{10}$-aryl radicals and unsubstituted $C_6$–$C_{10}$-aryl radicals, and X represents a member selected from the group consisting of Cl atoms, Br atoms, I atoms, acetate groups, dibenzylideneacetone groups and nitrate groups.

5. The process of claim 1, wherein the catalyst is a palladium complex of the general formula $L^1PdX_2$, wherein $L^1$ represents a chelating ligand of formula $R^4{}_2P(CH_2)_nPR^4{}_2$, in which $R^4$ is a member selected from the group consisting of substituted $C_1$–$C_{10}$-alkyl groups, unsubstituted $C_1$–$C_{10}$-alkyl groups, substituted $C_6$–$C_{10}$-aryl groups, unsubstituted $C_6$–$C_{10}$-aryl groups and n is from 1 to 4, and X represents a member selected from the group consisting of Cl atoms, Br atoms, I atoms, acetate groups, dibenylideneacetone groups and nitrate groups.

6. The process of claim 1, wherein the catalyst is a palladium(II) salt in combination with free ligands L or $L^1$, wherein L represents a member selected from the group consisting of phosphine bearing substituted $C_1$–$C_{10}$-alkyl groups, phosphine bearing unsubstituted $C_1$–$C_{10}$-alkyl groups, substituted $C_6$–$C_{10}$-aryl radicals and unsubstituted $C_6$–$C_{10}$-aryl radicals, and X represents a member selected from the group consisting of Cl atoms, Br atoms, I atoms, acetate groups, dibenzylideneacetone groups and nitrate groups, and $L^1$ represents a chelating ligand of formula $R^4{}_2P(CH_2)_nPR^4{}_2$, wherein $R^4$ is a member selected from the group consisting of substituted $C_1$–$C_{10}$-alkyl groups, unsubstituted $C_1$–$C_{10}$-alkyl groups, substituted $C_6$–$C_{10}$-aryl groups, unsubstituted $C_6$–$C_{10}$-aryl groups and n is from 1 to 4.

7. The process of claim 1, wherein the process is carried out at a temperature that is at least about 80° C.

8. The process of claim 1, wherein the process is carried out at a temperature that ranges from about 80° C. to about 140° C.

9. The process of claim 1, wherein the process is carried out at a pressure that is at least about 0.8 bar.

10. The process of claim 1, wherein the process is carried out at a pressure ranging from about 0.8 bar to about 5.0 bar.

11. The process of claim 1, wherein the process is carried out in a polar, aprotic, organic solvent.

12. The process of claim 1, wherein the process is carried out in dimethylformamide, N-methylpyrrolidone or dimethylacetamide.

13. The process of claim 1, wherein 4-trifluoromethoxybromobenzene is reacted.

14. The process of claim 1, wherein in the compounds having formulae (I), (II) and (III), $R^1$ is in meta position with respect to the $CH_2OHBr^-$ or $CHO^-$ group respectively.

15. The process of claim 14, wherein in the compounds having formulae (I), (II) and (III), $R^1$ is in meta position with respect to the $CH_2OH^-$, $Br^-$, $CHO^-$ or $CH_2$—$CH_2$—$NH_2$— group respectively.

16. A process for preparing benzyl alcohols of formula (I)

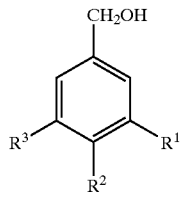

(I)

wherein each $R^1$, $R^2$ and $R^3$ is a member selected from the group consisting of H atoms, F atoms, Cl atoms, $NO_2$ groups, straight-chain or branched $C_1$–$C_{12}$-alkyl groups, phenyl groups, OH groups, $O(CH_2)_nCH_3$ groups, in which n=0–12, $(CF_2)_nCF_3$, in which n=0–2, or $O(CX_2)_nCX_3$, in which n=0–12, and X represents F and/or Cl;

the process comprising (A) reacting (1) aryl bromides of the general formula (II),

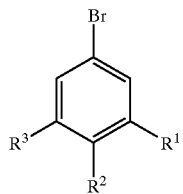

(II)

wherein $R^1$, $R^2$, $R^3$ are as defined for formula (I), with
(2) carbon monoxide and a formate in the presence of a palladium catalyst to form benzaldehydes of formula (III)

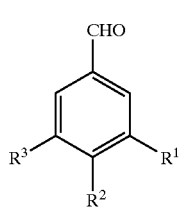

(III)

wherein $R^1$, $R^2$ and $R^3$ are as defined for formula (I), and (B) reducing the benzaldehydes of formula (III) to the corresponding benzyl alcohols, wherein the benzaldehydes of formula (III) are reacted directly, without intermediate work-up, with additional formate in the presence of a palladium catalyst to give benzyl alcohols of formula (I).

17. A process for preparing phenethylamines of formula (IV)

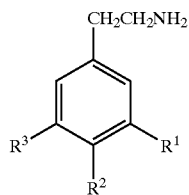

(IV)

wherein each $R^1$, $R^2$ and $R^3$ is defined as a member selected from the group consisting of H atoms, F atoms, Cl atoms, $NO_2$ groups, straight-chain or branched $C^1$–$C_{12}$-alkyl groups, phenyl groups, OH groups, $O(CH_2)_nCH_3$ groups in which n=0–12, $(CF_2)_nCF_3$ in which n=0–2 or $O(CX_2)_nCX_3$ in which n=0–12, and X represents F and/or Cl;

the process comprising (A) reacting (1) aryl bromides of the general formula (II),

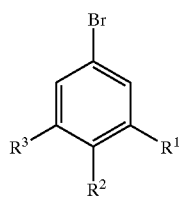

(II)

wherein each $R^1$, $R^2$ and $R^3$ is a member selected from the group consisting of H atoms, F atoms, Cl atoms, $NO_2$ groups, straight-chain or branched $C_1$–$C_{12}$-alkyl groups, phenyl groups, OH groups, $O(CH_2)_nCH_3$ groups, in which n=0–12, $(CF_2)_nCF_3$, in which n=0–2 or $O(CX_2)_nCX_3$, in which n=0–12, and X represents F and/or Cl, with (2) carbon monoxide and a formate in the presence of a palladium catalyst to form benzaldehydes of formula (III)

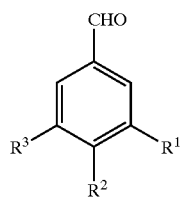

(III)

wherein $R^1$, $R^2$ and $R^3$ are as defined above, (B) reducing the benzaldehydes of formula (III) to the corresponding benzyl alcohols and forming a benzyl alcohol of formula (I)

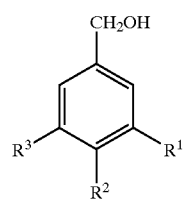

(I)

wherein the step of reducing the benzaldehydes of formula (III) is carried out using additional formate in the presence of a palladium catalyst, (C) reacting the benzyl alcohols of formula (I) with a halogenating reagent to form benzyl halides, (D) converting the benzyl halides to benzyl cyanides by reaction with cyanide, and (E) reducing the benzyl cyanides to phenethylamines of formula (IV).

18. A process for preparing phenethylamines of formula (IV)

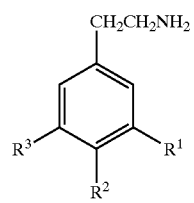

(IV)

wherein each $R^1$, $R^2$ and $R^3$ is defined as a member selected from the group consisting of H atoms, F atoms, Cl atoms, $NO_2$ groups, straight-chain or branched $C_1$–$C_{12}$-alkyl groups, phenyl groups, OH groups, $O(CH_2)_nCH_3$ groups in which n=0–12, $(CF_2)_nCF_3$ in which n=0–2 or $O(CX_2)_nCX_3$ in which n=0–12, and X represent F and/or Cl;

the process comprising:

(A) reacting (1) aryl bromides of the general formula (II),

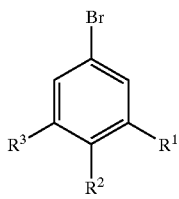

(II)

wherein $R^1$, $R^2$, $R^3$ are as defined for formula (I), with (2) carbon monoxide and a formate in the presence of a palladium catalyst to form benzaldehydes of formula (III)

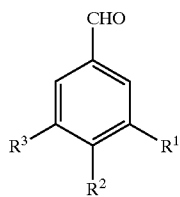

(III)

wherein each $R^1$, $R^2$ and $R^3$ is a member selected from the group consisting of H atoms, F atoms, Cl atoms, $NO_2$ groups, straight-chain or branched $C_1$–$C_{12}$- alkyl groups, phenyl groups, OH groups, $O(CH_2)_nCH_3$ groups in which n=0–12, $(CF_2)_nCF_3$ in which n=0–2 or $O(CX_2)_nCX_3$ in which n=0–12, and X represents F and/or Cl, (B) reducing the benzaldehydes of formula (III) to the corresponding benzyl alcohols, wherein the benzaldehydes of formula (III) are reacted directly, without intermediate work-up, with additional formate in the presence of a palladium catalyst to give benzyl alcohols of formula (I)

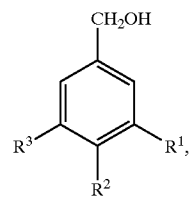

(C) reacting the benzyl alcohols of formula (I) with a halogenating reagent to form benzyl halides, (D) converting the benzyl halides to benzyl cyanides by reaction with cyanide, and (E) reducing the benzyl cyanides to phenethylamines of formula (IV).

* * * * *